United States Patent
Kawagishi

(10) Patent No.: US 6,464,642 B1
(45) Date of Patent: Oct. 15, 2002

(54) ULTRASONIC DIAGNOSIS APPARATUS

(75) Inventor: Tetsuya Kawagishi, Kuroiso (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/641,888

(22) Filed: Aug. 18, 2000

(30) Foreign Application Priority Data

Aug. 20, 1999 (JP) .......................................... 11-234439

(51) Int. Cl.$^7$ ................................................. A61B 8/06

(52) U.S. Cl. ....................... 600/454; 128/916

(58) Field of Search ................... 600/437, 440–497, 600/453–458, 407, 427; 395/119; 128/916

(56) References Cited

U.S. PATENT DOCUMENTS

| | | | | |
|---|---|---|---|---|
| 5,497,776 A | * | 3/1996 | Yamazaki et al. | 600/445 |
| 5,608,849 A | * | 3/1997 | King, Jr. | 395/119 |
| 5,776,067 A | * | 7/1998 | Kamada et al. | 600/443 |
| 6,208,883 B1 | * | 3/2001 | Holupka et al. | 600/407 |
| 6,256,529 B1 | * | 7/2001 | Holupka et al. | 600/427 |

FOREIGN PATENT DOCUMENTS

JP          9-253038          9/1997

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

The present invention provides an ultrasonic diagnostic apparatus and an ultrasonic image processing apparatus in which a three-dimensional region of interest (ROI) is clearly displayed by using a two-dimensional image while taking an advantage of a system for acquiring and displaying image data in a three-dimensional manner, and further, a three-dimensional position is set simply. This ultrasonic diagnostic apparatus comprises a 2D array probe for transmitting and receiving an ultrasonic wave for a diagnosis site of a patient's body in a three-dimensional manner, thereby obtaining a receiving signal; a apparatus main body for generating a three-dimensional image of a diagnosis site based on the thus obtained receiving signal; and a monitor for displaying a three-dimensional image thereof. In the apparatus main body, a display unit for setting a region of interest concerning diagnosis using a three-dimensional image, for setting a plurality of planes so as to include the region of interest, and for displaying an ultrasonic image of these plurality of planes is provided.

34 Claims, 11 Drawing Sheets

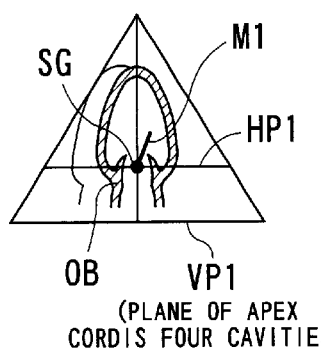
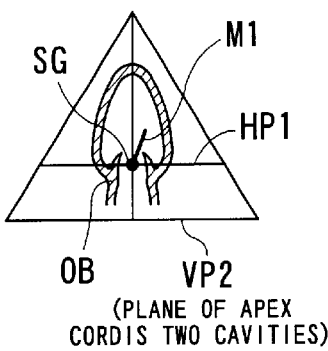
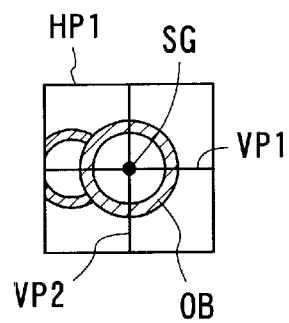
FIG. 6A  FIG. 6B  FIG. 6C
WHEN A LEFT-VENTRICLE WAVEFORM IS OBSERVED
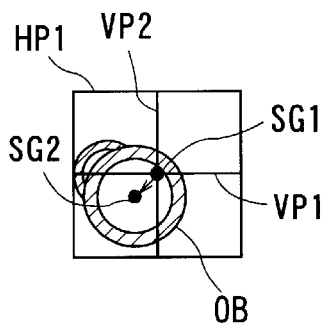
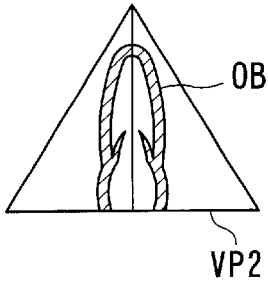
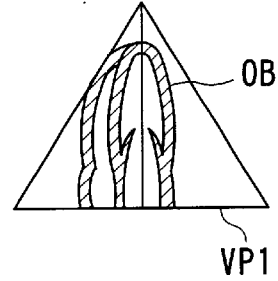
FIG. 7A  FIG. 7B  FIG. 7C
WHEN THE POSITION OF ORTHOGONAL TWO PLANES IS FIXED

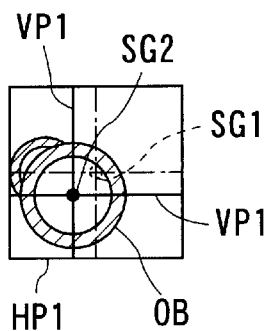
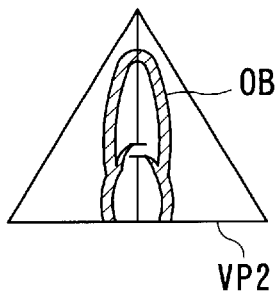
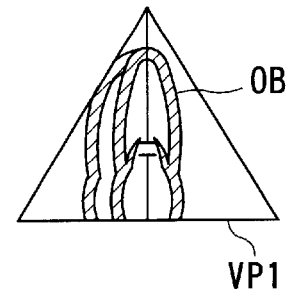
FIG. 8A   FIG. 8B   FIG. 8C
WHEN THE POSITION ORTHOGONAL TWO PLANES IS VARIABLE
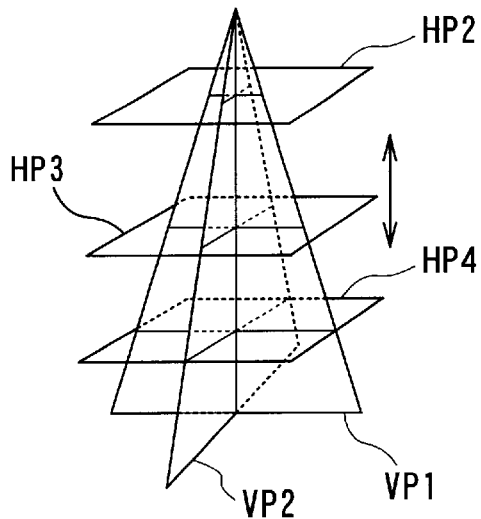
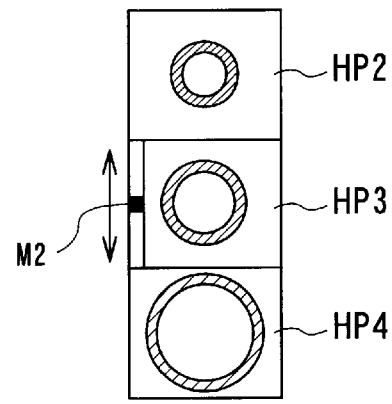
FIG. 9A   FIG. 9B

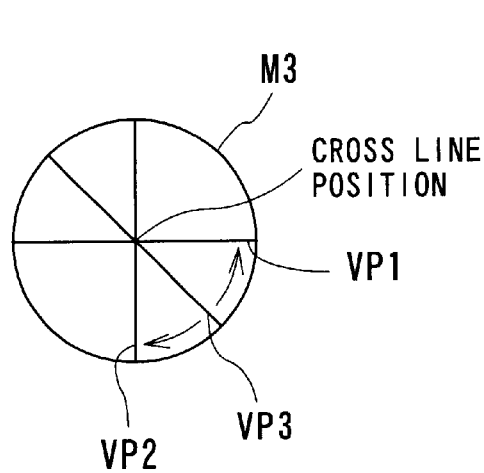
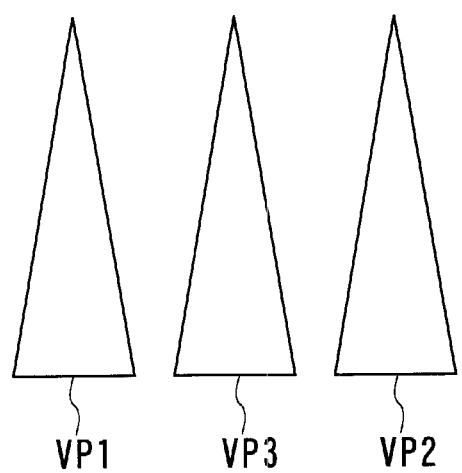
FIG. 10
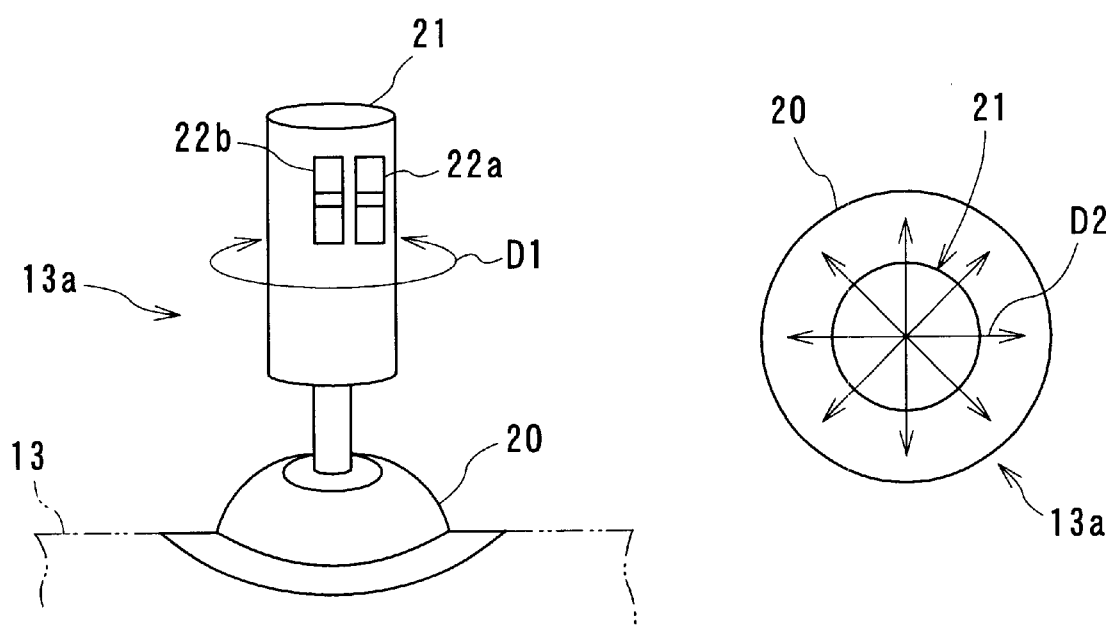
FIG. 11A  FIG. 11B

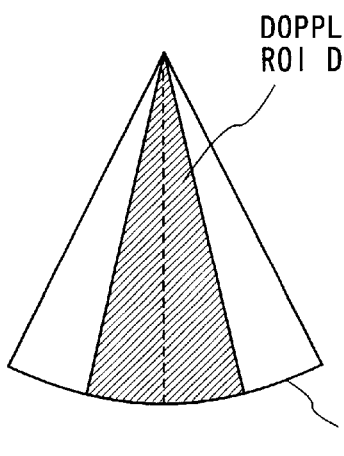
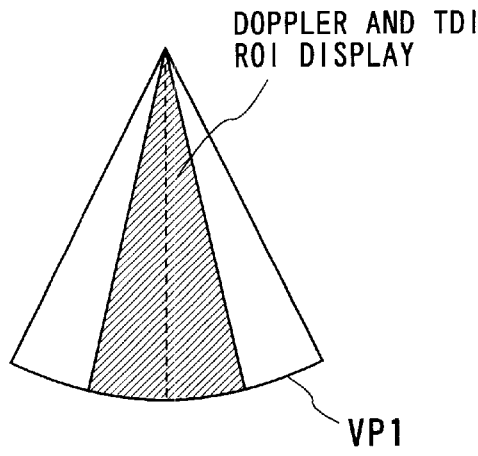
FIG. 13A  FIG. 13B
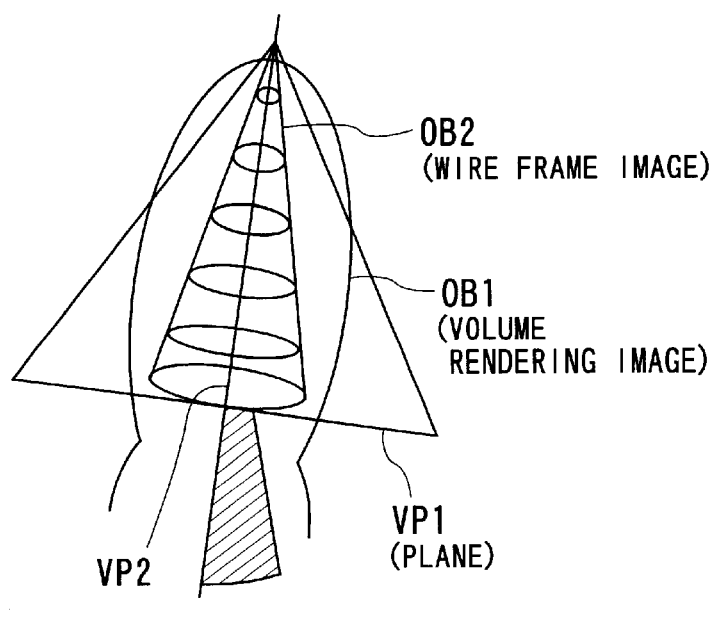
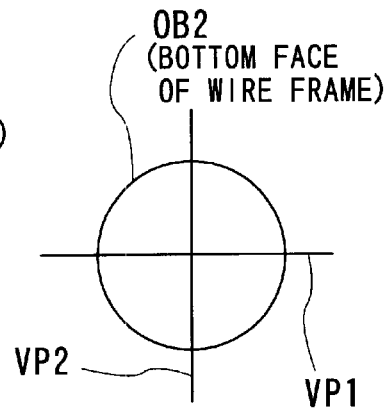
FIG. 14A  FIG. 14B

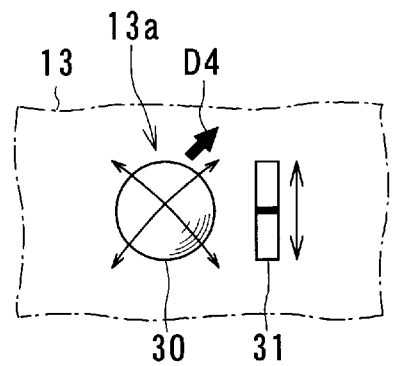 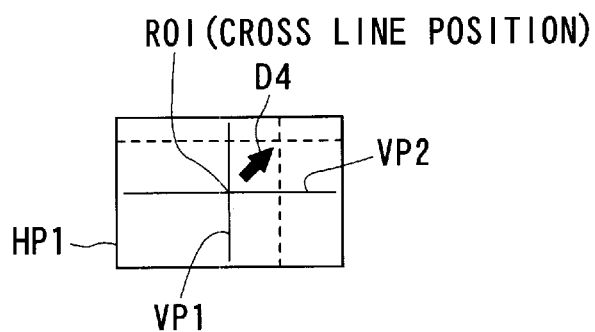
FIG. 16A          FIG. 16B
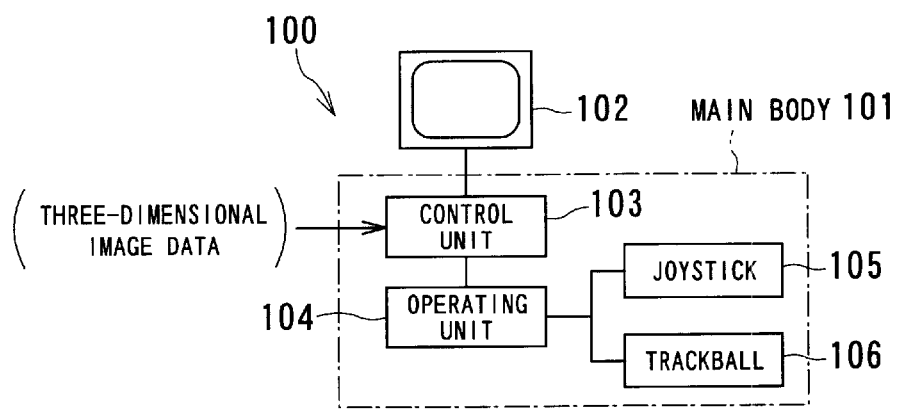
FIG. 17

ULTRASONIC DIAGNOSIS APPARATUS

BACKGROUND OF THE INVENTION

1. Field of the Invention

The present invention relates to an ultrasonic diagnostic apparatus for scanning ultrasonic beams to a diagnosis site such as a patient's heart in a three-dimensional manner, thereby acquiring image data in a three-dimensional manner, and displaying the three-dimensional image. In particular, the present invention relates to a modification in ROI (Region of Interest) setting and image display suitable to a case of performing a variety of measurements required for an ultrasound Doppler or examination using a three-dimensional image.

2. Description of Prior Art

In an ultrasonic diagnostic apparatus, ultrasonic Doppler imaging techniques such as Pulse Wave Doppler (PW), Continuous Wave Doppler (CW), Color Doppler Imaging (CDI), and Tissue Doppler Imaging (TDI) are generally performed. In the case where a variety of measurements required for diagnosis is performed for the image thus acquired, there is generally employed a technique for setting and specifying a desired target position by ROI while watching a two-dimensional image such as B-mode image displayed on a monitor. The technique using ROI in performing such PW, CW, CDI, and TDI or a variety of measurements are constructed while a two-dimensional image is presumed to be processed.

In contrast, in recent years, there is adopted a system for manually or mechanically moving a scan plane of an ultrasonic beam or employing a two-dimensional array probe to electronically scanning ultrasonic beams in real time, thereby spatially scanning the inside of a patient's body and acquiring three-dimensional physiological information.

In such a three-dimensional ultrasonic diagnostic apparatus for acquiring and displaying image data in a three-dimensional manner, if a technique employing a ROI constructed on assumption that a two-dimensional image is processed is applied as it is, there will occur a problem that a three-dimensional relative position between the patient's body and ROI is hardly clarified or ROI cannot be set simply in a three-dimensional manner.

SUMMARY OF THE INVENTION

The present invention has been made in view of the aforementioned conventional problem. It is an object of the present invention to clearly display a three-dimensional region of interest (ROI) using a two-dimensional image while taking an advantage of a system for acquiring and displaying image data in a three-dimensional manner, and further, to set a three-dimensional position simply.

In order to achieve the aforementioned object, an ultrasonic diagnostic apparatus according to the present invention comprises: ultrasonic wave transmitting and receiving means for transmitting and receiving an ultrasonic wave for a diagnostic site of the patient's body in a three-dimensional manner, thereby obtaining a receiving ultrasonic echo signal; data generating means for generating three-dimensional data based on the ultrasonic echo signal acquired by the ultrasonic wave transmitted and received by the ultrasonic wave transmitting and receiving means; display image generating means for obtaining ultrasonic images of a plurality of planes with their different orientations based on the three-dimensional image data generated by this data generating means, thereby generating the display image; a region of interest (ROI) setting means for setting a position of the region of interest (ROI); and plane position change means for changing a position of the plane so as to include the region of interest (ROI).

In the present invention, it is possible that the region of interest (ROI) is used for at least one of PW (Pulse Wave), CW (Continuous Wave), M-mode, CFM (Color Flow Mapping), TDI (Tissue Doppler Imaging), and image measurement.

In the present invention, it is possible that a position of the region of the interest (ROI) and a position of the plurality of planes are tracked with each other in real time.

In the present invention, it is possible that a plurality of planes are orthogonal to each other.

In the present invention, is possible that the plurality of planes include a first plane substantially parallel to a scanning line direction of the ultrasonic wave; a second plane substantially parallel to the scanning line direction of the ultrasonic wave and substantially orthogonal to the first plane; and a third plane substantially orthogonal to each of the first and second planes.

In the present invention, it is possible that the region of interest (ROI) setting means comprises a joystick. A lever of this joystick is moved in longitudinal direction, whereby the region of interest (ROI) moves on the first and third planes. The lever of the joystick is moved in horizontal direction, whereby the region of interest moves on the second and third planes. An input section mounted to the lever of the joystick is operated, whereby the region of interest (ROI) can be moved in a direction orthogonal to the third plane.

In the present invention, it is possible that the region of interest (ROI) setting means comprises a trackball. A ball of the trackball is moved, whereby the region of interest (ROI) moves in the third plane. In addition, an input section mounted in the vicinity of the trackball is operated, whereby the region of interest (ROI) moves in a direction orthogonal to the third plane.

An ultrasonic diagnostic apparatus according to another aspect of the present invention comprises: ultrasonic wave transmitting and receiving means for transmitting and receiving an ultrasonic wave for a diagnostic site of a patient's body in a three-dimensional manner, thereby obtaining a receiving ultrasonic echo signal; data generating means for generating three-dimensional image data based on the ultrasonic echo signal acquired by the ultrasonic wave transmitted and received by the ultrasonic wave transmitting and receiving means; display image generating means for obtaining ultrasonic images of a plurality of planes with their different orientations based on the three-dimensional image data generated by the data generating means, thereby generating a display image thereof; plane position change means for changing a position of said planes; and region of interest (ROI) setting means for setting a position of the region of interest (ROI) based on the position of plurality of planes.

An ultrasonic diagnostic apparatus according to another aspect of the present invention comprises: region of interest (ROI) setting means for setting a position of the region of interest (ROI); plane position change means for changing a position of a plurality of planes with their different orientations so as to include the region of interest; and display image generating means for transmitting and receiving an ultrasonic wave for a diagnosis site of the patient's body along the plurality of planes changed by the plane position change means to obtain the ultrasonic images of the plurality of planes, thereby generating a display image thereof.

An ultrasonic diagnostic apparatus according to another aspect of the present invention comprises: a plane position change means for changing a position of a plurality of planes with their different orientations; region of interest (ROI) setting means for setting a position of the region of interest (ROI) based on the position of the plurality of planes; and display image generating means for transmitting and receiving an ultrasonic wave for the diagnosis site of the patient's body along the plurality of planes changed by the plane position change means to obtain an ultrasonic image of the plurality of planes, thereby generating a display image thereof.

An ultrasonic diagnostic apparatus according to another aspect of the present invention comprises: ultrasonic wave transmitting and receiving means for transmitting and receiving an ultrasonic wave for a diagnosis site of the patient's body in a three-dimensional manner, thereby obtaining a receiving ultrasonic echo signal; data generating means for generating three-dimensional image data based on the ultrasonic echo signal acquired by the ultrasonic wave transmitted and received by the ultrasonic wave transmitting and receiving means; display image generating means for obtaining ultrasonic images of a plurality of planes with their different orientations based on the three-dimensional image data generated by the data generating means, thereby generating a display image thereof; setting means for setting a cross line position among the plurality of planes, and plane position change means for changing the position of the planes so as to include the cross line position.

An ultrasonic diagnostic apparatus according to another aspect of the present invention comprises: ultrasonic wave transmitting and receiving means for transmitting and receiving an ultrasonic wave for the diagnostic site of the patient's body in a three-dimensional manner, thereby obtaining a receiving ultrasonic echo signal; data generating means for generating three-dimensional image data based on the ultrasonic echo signal acquired by the ultrasonic wave transmitted and received by the ultrasonic wave transmitting and receiving means; display image generating means for obtaining ultrasonic images of a plurality of planes with their different orientations based on the three-dimensional image data generated by the data generating means, thereby generating a display image thereof; plane position change means for changing a position of the planes; and setting means for setting the cross line position based on the position of the plurality of planes.

An ultrasonic image processing apparatus according to the present invention comprises: display image generating means for obtaining ultrasonic images of a plurality of planes with their different orientations based on three-dimensional ultrasonic image data of the diagnosis site of the patient's body, thereby generating a display image thereof; region of interest (ROI) setting means for setting a position of the region of interest (ROI); and plane position change means for changing a position of the planes so as to include the region of interest.

An ultrasonic image processing apparatus according to another aspect of the present invention comprises: display image generating means for obtaining ultrasonic images of a plurality of planes with their different orientations based on three-dimensional ultrasonic image data of the diagnosis site of the patient's body, thereby generating a display image thereof; plane position change means for changing a position of the planes; and region of interest (ROI) setting means for setting a position of the region of interest (ROI) based on the position of the plurality of planes.

As has been described above, according to the present invention, a three-dimensional region of interest (ROI) can be clearly displayed by using a plurality of tomographic images (two-dimensional images) while taking advantage of a system for acquiring and displaying image data in a three-dimensional manner. In this manner, there can be provided an ultrasonic diagnostic apparatus and an ultrasonic image processing apparatus in which a position in a three-dimensional space of the region of interest can be clearly displayed in a variety of image modes or measurement, and a three-dimensional region of interest (ROI) can be easily set in a three-dimensional space.

BRIEF DESCRIPTION OF THE DRAWINGS

The other configuration and advantageous effect according to the present invention becomes apparent from a description taken in conjunction with the following embodiments of the invention and the accompanying drawings in which:

FIG. 6A to FIG. 6C are schematic views each illustrating an example of displaying a plurality of planes when a left-ventricle outflow waveform of the heart is observed;

FIG. 7A to FIG. 7C are schematic views each illustrating a display example when two orthogonal planes are fixed;

FIG. 8A to FIG. 8C are schematic views each illustrating a display example when two orthogonal planes are variable;

FIG. 9A and FIG. 9B are schematic views each illustrating an example of setting three horizontal planes;

FIG. 10A and FIG. 10B are schematic views each illustrating an example of setting three vertical planes;

FIG. 11 illustrates an outline of a joystick, in which FIG. 11A is a schematic side view of the joystick and FIG. 11B is a schematic top view of the joystick;

FIG. 13A and FIG. 13B are conceptual views each illustrating an example of ROI display for Doppler and TDI imaging;

FIG. 14A and FIG. 14B are conceptual views each illustrating a display example when the three-dimensional shape of ROI is important;

FIG. 16A and FIG. 16B are a view illustrating an operational example of trackball; and FIG. 17 is a schematic view showing an ultrasonic image processing apparatus.

DETAILED DESCRIPTION OF THE PREFERRED EMBODIMENTS

Hereinafter, preferred embodiments of an ultrasonic diagnostic apparatus according to the present invention will be described with reference to the accompanying drawings.

Figure 1:
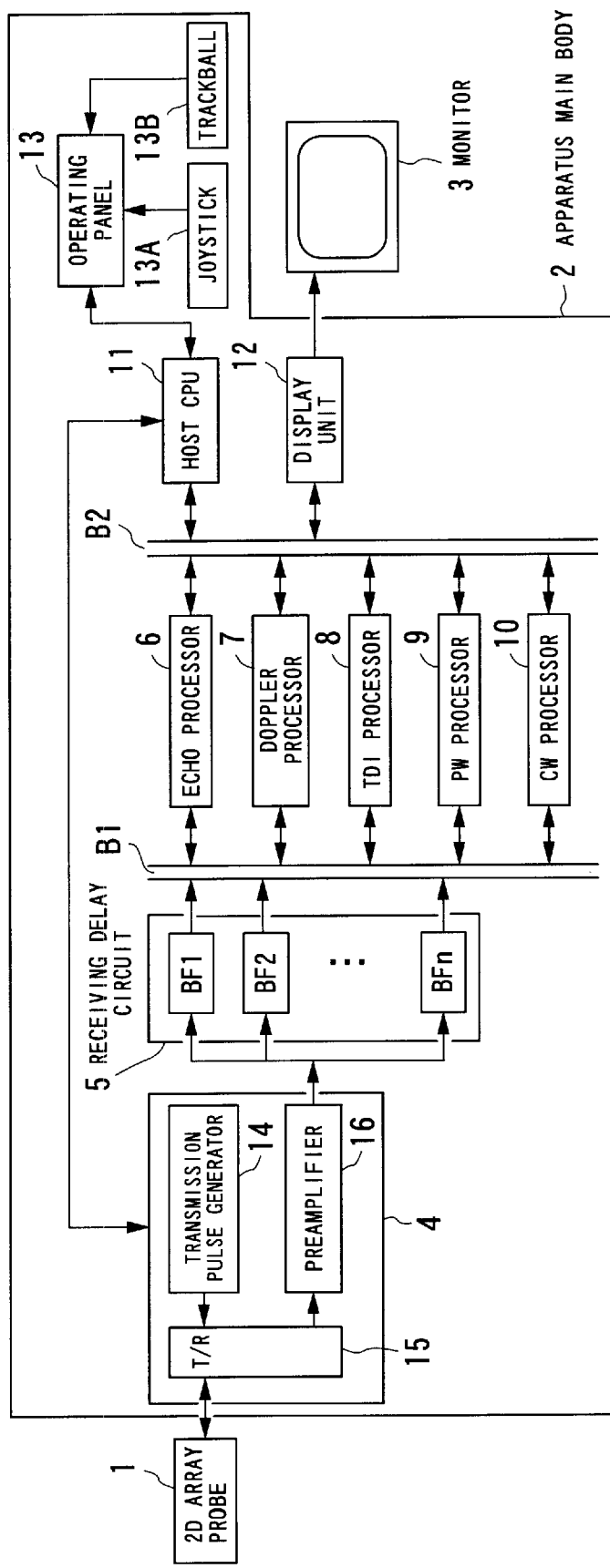
FIG. 1 is a schematic block diagram depicting an entire configuration of a three-dimensional ultrasonic diagnostic apparatus according to one embodiment of the present invention.

An ultrasonic diagnostic apparatus shown in FIG. 1 is achieved by applying a system for scanning ultrasonic beams spatially, thereby acquiring a three-dimensional image thereof in real time. This apparatus comprises a two-dimensional array probe 1 capable of spatially scanning ultrasonic beams; an apparatus main body 2 having this probe 1 connected thereto; and a monitor 3 connected to this apparatus main body 2.

The two-dimensional array probe 1 has a plurality of ultrasonic oscillators (not shown) arrayed thereon in two-dimensional array manner. These ultrasonic oscillators each are driven under the control of the apparatus main body 2, whereby ultrasonic beams are scanned in a three-dimensional manner toward the diagnosis site in the patient's body in accordance with preset transmission beam forming conditions. In addition, an ultrasonic echo signal returned to the probe 1 due to the reflection on the acoustic impedance interface in the patient's body relevant to the ultrasonic beams or the scattering due to a fine scattering body is received by being converted into a fine voltage echo signal; and the receiving signal is fed to the apparatus main body 2.

The apparatus main body 2 comprises a pulser/preamplifier 4 connected to the probe 1; a receiving signal delay circuit 5 connected to a preamplifier output of this unit 4; a plurality of processors, i.e., echo processor 6, Doppler processor 7, TDI processor 8, PW processor 9, and CW processor 10 connected to this delay circuit 5 via a first bus B1; a host CPU 11 and a display unit 12 that are connected to each of these processors 6 to 10 via a second bus B2; and a operating panel 13 connected to the host CPU 11.

On the operating panel 13, there is mounted input devices (such as switches, buttons, keyboard) including a joystick 13a for setting or changing ultrasonic beam transmitting and receiving conditions or the like or trackball 13b or the like. Information instructed by an operator is sent to the host CPU 11 through the input operation, whereby the above conditions are set or changed at each section inside of the apparatus main body 2. For example, in the case of pulse Doppler imaging such as heart is performed, an operator operates a joystick 13a while seeing the screen of a monitor 3, whereby the position of a sample gate corresponding to ROI can be set or changed.

The pulser/preamplifier unit 4 comprises a transmission pulse generator 14, T/R (transmitter/receiver) 15, and a preamplifier 16. A pulse voltage for controlling the direction and convergence of ultrasonic beams by the probe 1 is generated based on the three-dimensional transmission beam forming conditions preset by the transmission pulse generator 14 under the control of the host CPU 11. Then, a drive signal based on this pulse voltage is supplied to the probe 1 via a transmitter of T/R15, and the receiving signal from the probe 1 is amplified by a preamplifier 16 via a receiver of T/R 15, and this amplified signal is fed to a reception delay circuit 5.

The reception delay circuit 5 comprises a plurality of beam formers BF1 to BFn capable of performing parallel and simultaneous reception in response to a receiving signal from the preamplifier 16. A reception delay is applied at each of these beam formers BF1 to BFn so as to meet conditions for the direction and convergence of ultrasonic beams in three-dimensional reception beam forming preset for each reception signal. Then, this delay signal is supplied to the processors at the next stage.

The echo processor 6 undergoes orthogonal wave detection using a predetermined reference frequency in response to a receiving signal from the reception delay circuit 5. Then, the echo processor 6 generates three-dimensional spatial distribution image data indicating three-dimensional information (contract image including information on contrast medium when administered) in the patient's body according to a signal amplitude of the wave detected signal, and feeds this image data to a display unit 12.

The Doppler processor 7 measures a change in phase with time in response to the receiving signal from the reception delay circuit 5, thereby generating three-dimensional spatial distribution image data such as velocity, power and dispersion indicating blood flow information of the patient's body. Then, this image data is sent to the display unit 12.

The TDI processor 8 measures a change in phase with time in response to the receiving signal from the reception delay circuit 5, thereby generating three-dimensional spatial distribution image data such as movement velocity, power and dispersion of the tissue of the patient's body. Then, this image data is sent to the display unit 12.

The PW processor 9 operates during pulse Doppler imaging, detects a receiving signal corresponding to a position in a sample gate range internally instructed to a signal from the reception delay circuit 5, and Fourier-transforms the detected signal, whereby the Doppler frequency distribution of the velocity in the sample gate is computed, and the computation result is fed to the display unit 12.

The CW processor 10 operates during continuous wave Doppler imaging, detects a receiving signal corresponding to a position on a sample line internally instructed to a signal from the reception delay circuit 5, and Fourier-transforms the detected signal, whereby the Doppler frequency distribution of the velocity on the sample line is computed, and the computation result is fed to the display unit 12.

The display unit 12 generates a plurality of two-dimensional tomographic images along a plurality of tomographic planes preset in image processing such as MPR (Multi Planar Reconstruction) for three-dimensional image data or the like from each of the aforementioned processors 6 to 10 under the control of the host CPU 11. Then, the display unit 12 displays these tomographic images on a monitor 3 together with single or various three-dimensional images.

In addition, this display unit 12 sets a position of a plane or a position of the ROI at which a plurality of two-dimensional tomographic images should be displayed based on the ROI information when information concerning ROI such as sample gate is inputted via the host CPU 11 by operating the joystick 13a or the like of an operating panel 13 while an operator is watching the display image on the monitor 3, whereby ultrasonic Doppler or measurement and the like can be performed. Information such as ROI shape or position can be set or changed by the operating panel 13.

Here, a description of an entire operation will be given with reference to the accompanying drawings, while focusing on an example of setting the ROI by means of the display unit 12. Here is exemplified a case in which pulse Doppler imaging is performed for the heart presumed as an examination site in the patient's body. The ROI corresponds to "a sample gate" on a raster (sample line) of ultrasonic beams.

Figure 2:
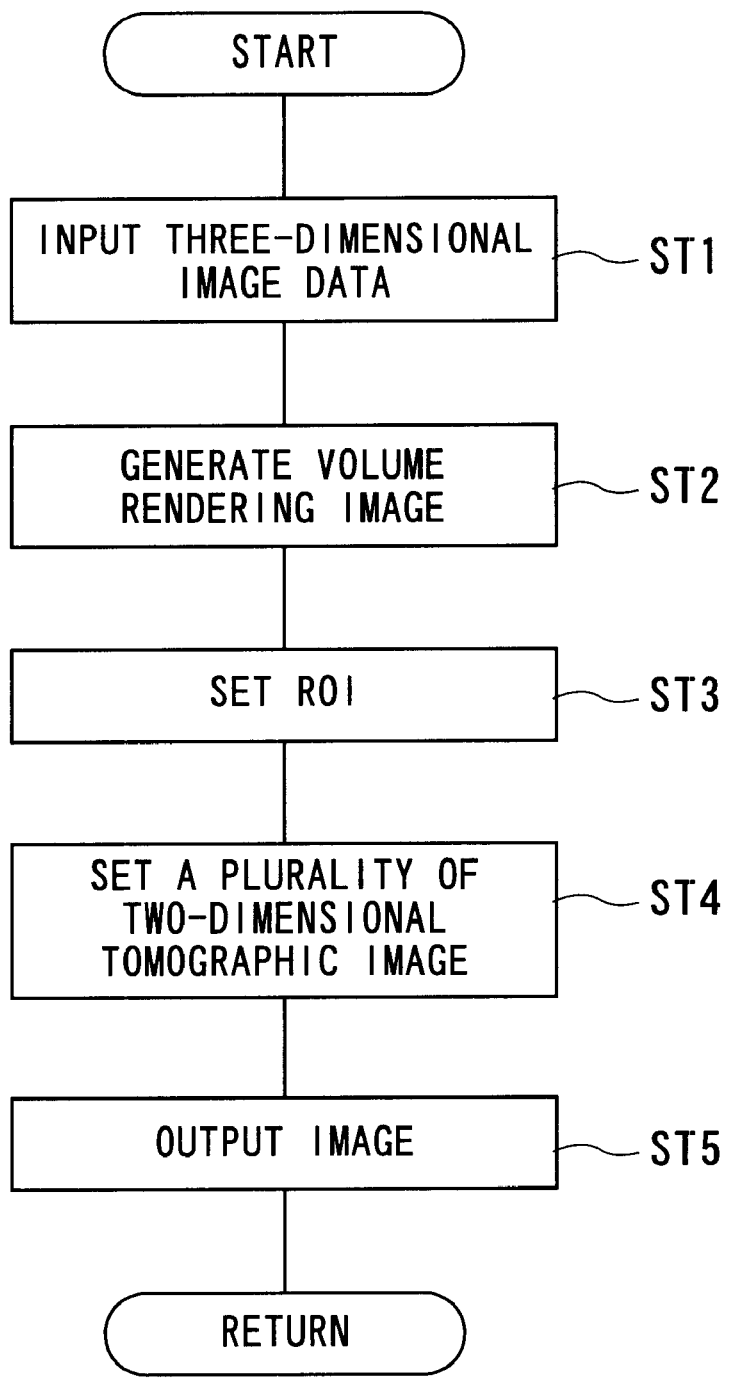
FIG. 2 is a schematic flow chart illustrating processing of a display unit.

When the apparatus is first driven, ultrasonic beams from the two-dimensional array probe 1 are scanned in a three-dimensional manner toward the heart in the patient's body, whereby three-dimensional image data is acquired in the apparatus main body 2 in real time. In parallel to this scanning, the processing shown in FIG. 2 is executed by means of the display unit 12.

That is, when the aforementioned three-dimensional image data is inputted at step ST1, a volume rendering image that is one of the typical three-dimensional images for the heart, for example, is generated at step ST2. This volume rendering image is displayed on the monitor 3 as required.

Then, at step ST3, in the case of ROI, that is, pulse Doppler imaging, a sample gate is set. This sample gate is set as this ROI based on the operator's instruction information inputted from the operating panel 13 via the host CPU 11. A plurality of plane positions are set according to the position of the sample gate instructed above at step ST4, and two-dimensional tomographic images of the plurality of planes are generated by MPR. These generated images are outputted at step ST5, whereby a plurality of tomographic images are displayed on the screen of the monitor 3.

Figure 3:
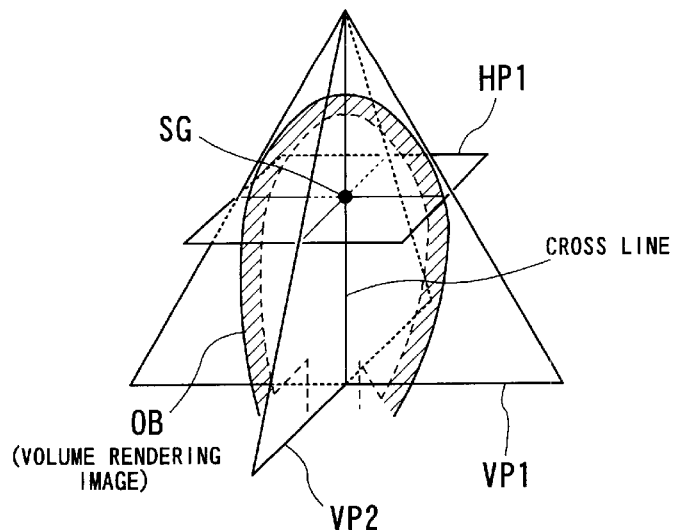
FIG. 3 is a conceptual view illustrating an example of displaying a volume rendering image and a plurality of plane positions of the heart.
Figure 4A:
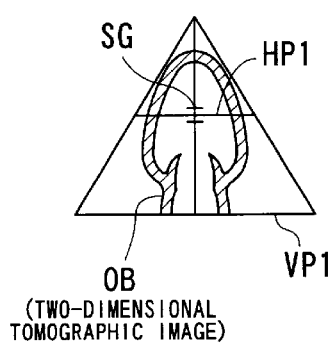
FIG. 4A to FIG. 4C are conceptual views each illustrating an example of displaying a plurality of planes when a pulse Doppler imaging of the heart is performed.
Figure 4B:
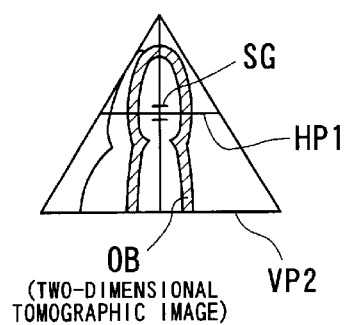
Figure 4C:
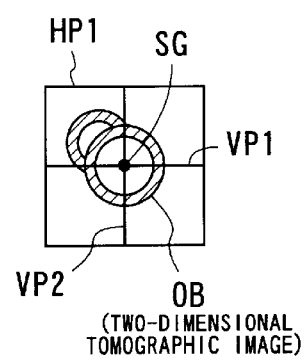
Figure 5:
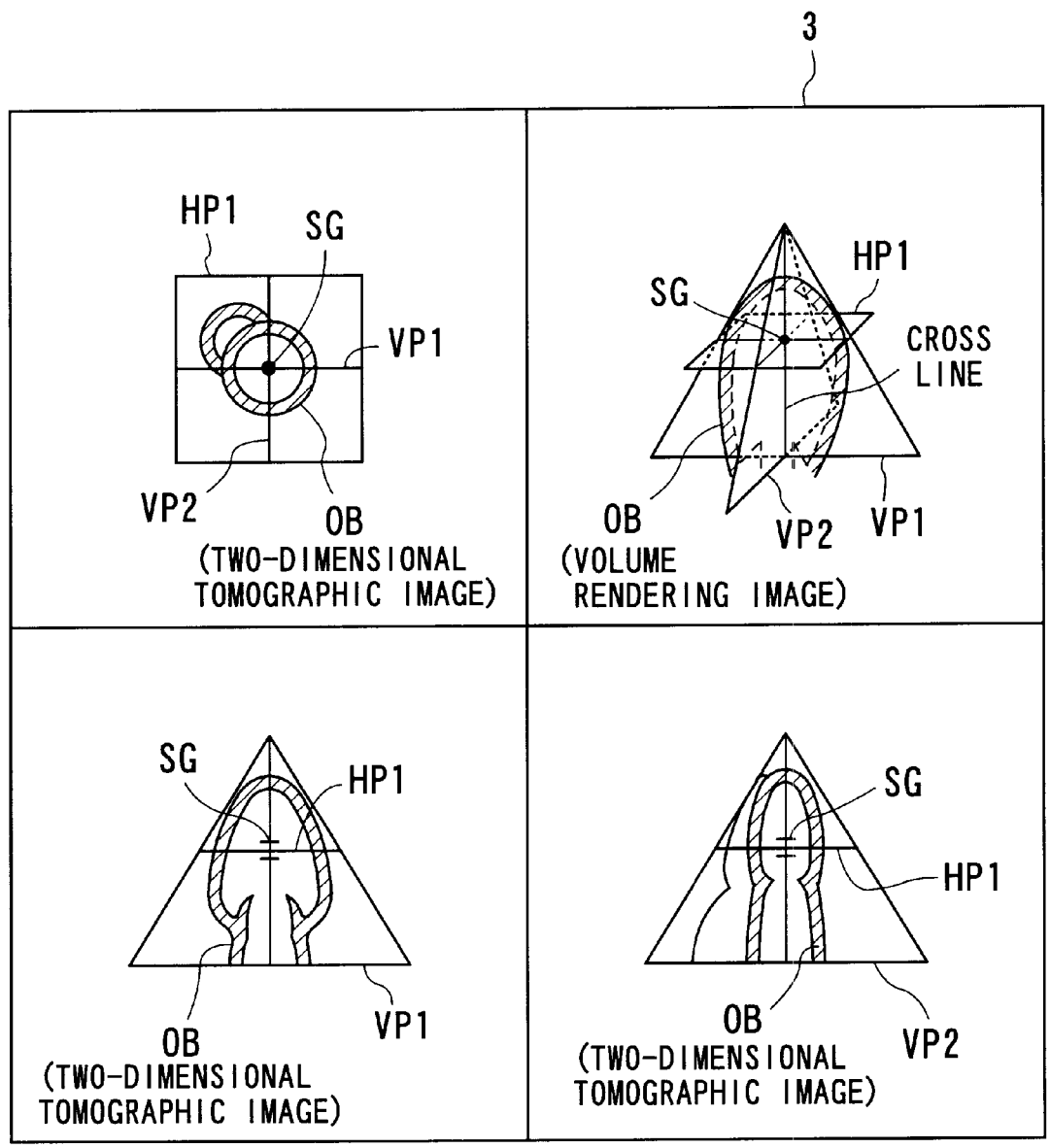
FIG. 5 is a view illustrating an example of displaying a plurality of planes on a monitor.

FIG. 3 shows an example of displaying a volume rendering image (three-dimensional image) of the heart OB and a plurality of plane positions set in that image. FIG. 4A to FIG. 4C each show an example of the sample gate SG and two-dimensional tomographic image (B-mode image) on a plurality of planes set in the three-dimensional image shown in FIG. 3. FIG. 5 shows an example of the display screen on the monitor 3 for ultrasonic images of these plurality of planes.

A plurality of planes shown in FIG. 4A to FIG. 4C include two orthogonal planes VP1 and VP2 on which a straight line between a oscillator face of the probe 1 and a sample gate SG on a sample line is defined as a cross line (Refer to FIG. 4A and FIG. 4B. This plane corresponds to a "first plane" and a "second plane" of the present invention. Hereinafter, referred to as a "vertical plane" for the sake of convenience); and a plane HP1 orthogonal to the cross line at a position of the sample gate on the cross line on these two vertical planes (Refer to FIG. 4C. This plane corresponds to a "third plane" of the present invention. Hereinafter, referred to as a "horizontal plane" for the sake of convenience). The cross line position of each of these planes is displayed in order to more clarify the relative position each other as illustrated.

In FIG. 5, the ultrasonic images of the vertical planes VP1 and VP2 orthogonal to each other shown in FIG. 4A and FIG. 4B are displayed horizontally in an region at the lower part of the screen of the monitor 3; ultrasonic images of the horizontal planes HP1 shown in FIG. 4C is displayed horizontally in an region at the upper part of the screen; and volume rendering images shown in FIG. 3 are displayed horizontally, respectively. The display positions of these four images can be changed conveniently at a position at which an operator can be easily seen without being limited thereto.

With respect to the aforementioned position of each plane, in the case where the left-ventricle outflow waveform of the heart is observed, as shown in FIG. 6A to FIG. 6C, it is preferable that one of these two vertical planes VP1 and VP2 is set as a plane of apex cordis four cavities (refer to FIG. 6A) that passes in the vicinity of the apex cordis four cavities of the heart OB; the other is set as a plane of apex cordis two cavities (refer to FIG. 6B) that passes in the vicinity of the apex cordis two cavities of the heart OB; and a horizontal plane HP1 is preferably set as a plane when the vicinity of the valve contour portion of the heart OB is defined as a sample gate SG, respectively. This is because a three-dimensional relative position relationship between the sample gate SG and the heart OB can be easily grasped.

In each of the planes shown in FIG. 6A to FIG. 6C, a Doppler angle correction marker Ml can be displayed and corrected, thereby making it possible to take an advantage of a real-time three-dimensional ultrasonic diagnostic apparatus capable of performing three-dimensional Doppler angle correction.

In consideration of a case in which the positions of the above-described vertical planes VP1 and VP2 and the horizontal plane HP1 are adjusted in a three-dimensional manner (Refer to means using a joystick which will be described later), a case in which these positions can be variably set automatically or manually at a desired position as required is more desirable than a case in which the positions are fixedly set. The reason will be described with reference to FIG. 7 and FIG. 8 by way of showing an example of two vertical planes (orthogonal two planes) VP1 and VP2.

First, a case in which the positions of two vertical planes VP1 and VP2 are fixed will be described with reference to FIG. 7A to FIG. 7C. Here, assume that the sample gate position is moved from SG1 shown in the figures to SG2 in the horizontal plane HP1 shown in FIG. 7A. In this case, the positions of the two vertical planes VP1 and VP2 are fixed when the position SG1 before sample gate movement is defined as a reference. Thus, the position SG2 after the movement is not displayed on the vertical planes VP1 and VP2, making it difficult to grasp a three-dimensional position.

In contrast, a case in which the positions of the two vertical planes VP1 and VP2 are variably set automatically in conformance to the sample gate movement will be described with reference to FIG. 8A to FIG. 8C. Here, assume that the sample date position is moved from SG1 shown in the figure to SG2 in the transverse face HP1 shown in FIG. 8A in the same way as the above. In this case, the positions of the two vertical planes VP1 and VP2 are set to be varied faithfully along a vector from SG1 to SG2 according to sample gate movement. Therefore, in this case, the ROI can always be displayed on each of the tomographic images of the two vertical planes VP1 and VP2, whereby a relative position relationship between the ROI and the heart can be grasped in a three-dimensional manner irrespective of sample gate movement.

In this case, although a plurality of planes are automatically displayed faithfully while a sample gate is tracked, it is possible to provide settings so that a position is changed independent of such sample gate as required. In addition, if the depth of the sample gate is changed, it is possible to provide settings so that the horizontal plane HP1 is variable faithfully according to the depth.

In the above example, although there has been described a case in which a plurality of planes VP1, VP2, and HP1 are orthogonal to each other, respectively, the present invention is not limited thereto. For example, two vertical planes VP1 and VP2 may not be orthogonal to each other. In addition, a straight line connecting the probe 1 and the sample gate SG may not coincide with a cross line of the vertical planes VP1 and VP2. Further, the horizontal plane HP1 may not always include a sample gate SG. In this case, a position at which the sample gate SG is projected may be displayed.

Of course, the present invention is applicable to three or more planes. For example, in the above example, although three-dimensional image information is displayed as an image using three planes for the sake of clarity, the tomographic image displayed in this case is a part of the three-dimensional image. Therefore, three planes are insufficient depending on a diagnosis site or its purpose, and a case in which much more information is required is presumed. A preferable example of this case will be described with reference to FIG. 9 and FIG. 10.

FIG. 9A and FIG. 9B each illustrate an example of setting three or more planes generated by MPR. In a plurality of planes shown in FIG. 9A and FIG. 9B, any position can be changed in accordance with a sample gate. These planes include the two vertical planes (planes for B-mode tomographic images) VP1 and VP2 and three horizontal planes HP2, HP3, and HP4 set parallel to each other at a predetermined position on the cross line with constant intervals.

The horizontal plane HP3 positioned at the center in the three horizontal planes is set so that the position can be changed while reciprocating movement is repeated between two horizontal planes HP2 and HP4 positioned on its both sides at a constant speed. In this manner, an image at the changed position is displayed so that many more three-dimensional images can be provided. The relative position of the horizontal plane HP3 at the center can be displayed by a marker M2 movable in a vertical direction between two horizontal planes HP2 and HP4 shown in FIG. 9B, for example.

FIG. 10A and FIG. 10B each illustrate a case in which the aforementioned vertical planes VP1 and VP2 and new vertical plane VP3 passing through this cross line are added. In this case, the relative position of the newly added vertical plane VP3 rotates around the cross line as indicated by the marker M3 shown in FIG. 10A, and is set changeably. In this manner, as shown in FIG. 10B, an image is displayed at the changed position so that many more three-dimensional images can be provided. In this case, the two vertical planes VP1 and VP2 orthogonal to each other move in parallel to each other while a mutual angle is kept to be constant, thereby making it possible to set the corresponding image to be displayed.

Now, a method for displaying a sample gate on the aforementioned plurality of planes will be described with reference to an example of means for moving and setting the sample gate in a three-dimensional space. In general, in diagnosis performed using an ultrasonic diagnostic apparatus, there often exists only one operator. During the diagnosis, one hand (arm) is used to apply the probe to the patient. With respect to sample gate setting other than operation for applying the probe to the patient, it is desirable that such setting can be operated as simple as possible by using the other hand (arm). Therefore, a setting example when a joystick 13a operable by one hand is used, thereby the sample gate is moved in a three-dimensional manner will be described with reference to FIG. 11 and FIG. 12.

Figure 12A:
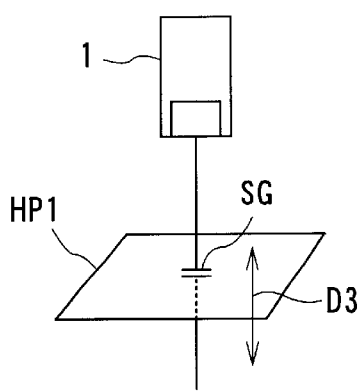
FIG. 12A to FIG. 12C are schematic views each illustrating an example of moving and setting a sample gate and a plurality of planes according to an operation of the joystick shown in FIG. 10.

The joystick 13a comprises a joystick mount section 20 installed at a predetermined position on the operating panel 13, for example, as shown in FIG. 11A and FIG. 11B; and a rod-like joystick main body (lever) 21 mounted to this joystick mount section 20. This lever 21 is set in a longitudinal or transverse direction and in any direction within the range of 360 degrees in a horizontal direction (Refer to the direction indicated by the arrow D2 shown in FIG. 11B) or is rotated around the axial direction of the lever as indicated by the arrow D1 shown in FIG. 11A, thereby making it possible to move or set the sample gate SG as shown in FIG. 12A to FIG. 12C.

Figure 12B:
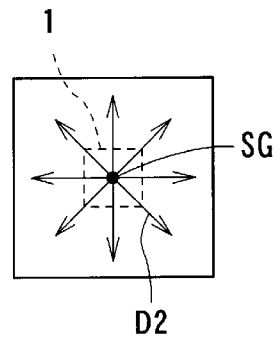
Figure 12C:
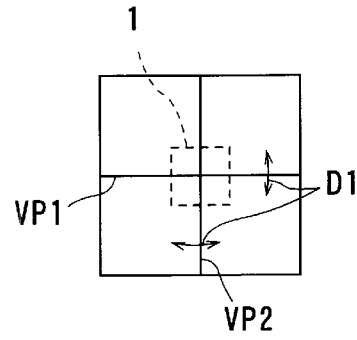

For example, when the lever 21 is set in the direction indicated by the arrow D2 shown in FIG. 11B, the sample gate SG is moved and set in the direction indicated by the arrow D2 shown in FIG. 12B. In addition, when the lever 21 is rotated in the direction indicated by the arrow D1 shown in FIG. 11 A, the mutually orthogonal vertical planes VP1 and VP1 for B-mode tomographic image are rotated and set around a cross line as shown in FIG. 12C apart from sample gate movement.

In addition, first and second input sections 22a and 22b are mounted to the lever 21 as shown in FIG. 11A. For example, the depth of the sample gate SG is changed suitably by operation of the first input section 22a as indicated by the arrow D3 shown in FIG. 12A. Alternatively, the size of the sample gate SG can be changed suitably by operation of the second input section 22b.

Therefore, according to the illustrative embodiment, a three-dimensional ROI can be clearly displayed using a plurality of tomographic images while taking an advantage of a system for acquiring and displaying image data in a three-dimensional manner. In this manner, a position in a three-dimensional space of the ROI can be easily grasped in a variety of modes or measurement.

In the illustrative embodiment, although image display, operating method or the like has been described by exemplifying a three-dimensional image for the heart as a diagnosis site and a sample gate of pulse Doppler imaging as a ROI, the present invention is not limited thereto.

The displaying and operating means that is similar to the aforementioned means is equally effective to continuous wave Doppler, M-mode, Color Doppler Imaging (CDI), Tissue Doppler Imaging (TDI), a variety of measurement or any other diagnosis sites targeted by using the ultrasonic diagnostic apparatus. In this case, it is desirable to automatically move a plane together with ROI movement so that all of the ROI or its center and/or interface is always clearly displayed on a plane.

For example, in the case of Continuous Wave Doppler or M-mode Imaging, a cross line of the orthogonal planes is set so as to always coincide with a sample line, whereby an image is displayed more clearly.

In addition, in the case of Color Doppler or Tissue Doppler Imaging, a cross line of a plurality of planes is set so as to pass through the center of gravity of the region of interest for Doppler always specified as a three-dimensional space, thereby an image is displayed more clearly. An example is shown in FIG. 13A and FIG. 13B.

In the figures, a plane shape indicating the region of interest for Color Doppler or Tissue Doppler Imaging can be displayed on vertical planes VP1 and VP2 of a plurality of tomographic images generated by MPR.

Further, the displaying and operating means that is similar to the above is effective t6 simple distance measurement or three-dimensional ROI setting. For example, in the case of distance measurement, the segment of line may be fully displayed on any of these planes.

In addition, in the case of Color Doppler or Tissue Doppler Imaging or any other measurement, the three-dimensional shape of the ROI is important. When information on a portion that is not displayed in a tomographic image is required, as shown in FIG. 14A, a wire frame image OB2 is displayed as a ROI in a volume rendering image OB1 together with the position display of a plurality of the two-dimensional tomographic image planes VP1 and VP2. Then, as shown in FIG. 14B, the positions of the vertical planes VP1 and VP2 are set so as to include the bottom face of a wire frame image OB2, and the positions of the vertical planes VP1 and VP2 can be moved together with a change in wire frame image OB2.

In the case of a three-dimensional ROI, switches, lever, and buttons can be disposed at the lever 21 of the joystick 13a shown in FIG. 11A described previously or its periphery for the purpose of adjustment tailored for the ROI size, shape measurement, and image mode. Although all operations can be performed by one hand, a foot pedal or the like is provided as one means for avoiding difficulty in this one-hand operation, thereby making it possible to cause some of the operations.

Further, when the region of interest is a tomographic image itself, the aforementioned setting means is more effective in setting a plane to be reconstructed by MPR using three-dimensional image information. For example, the lever 21 of the joystick 13a is operated, whereby there may be moved two orthogonal vertical planes VP1 and VP2 and the position of a horizontal HP1 orthogonal to each of these vertical planes VP1 and VP2. Specifically, when the joystick 13a is moved in longitudinal or transverse direction, the respective vertical planes VP1 and VP2 move so that the cross line position between the two vertical planes VP1 and VP2 moves accordingly. When the joystick 13a is rotated in a torsion direction, each plane is rotated around a cross line position. When an input section 22a mounted to the joystick 13a is operated vertically, the horizontal plane HP1 moves along the vertical direction of the cross line of the vertical planes VP1 and VP2. In this manner, it is possible to move the position of each plane in accordance with movement of the cross line of a plurality of planes without using the region of interest (ROI).

FIG. 15A to FIG. 15E each illustrate an example of a technique to clarify a position relationship between the operating direction such as longitudinal or transverse direction of the joystick 13a and the direction of each of the aforementioned VP1 and VP2.

Figure 15A:
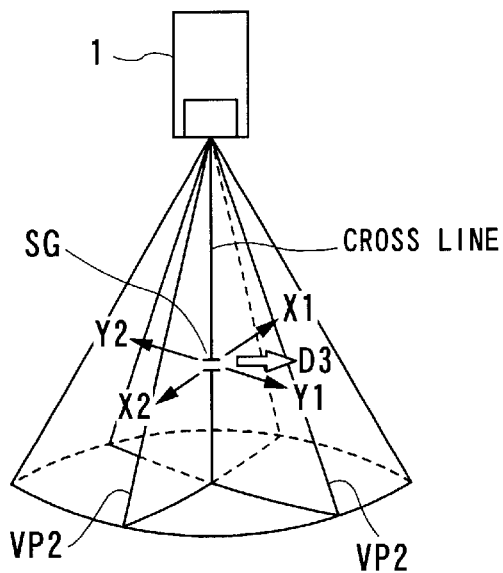
FIG. 15A to FIG. 15E are views each showing an example of correlation between a direction of a plurality of planes and a joystick operation direction.

In FIG. 15A, in a three-dimensional ultrasonic scan region using the probe 1, the X1 and X2 directions opposite to each other are set in a direction parallel to the aforementioned vertical plane VP1; and the Y1 and Y2 directions opposite to each other are set in a direction parallel to the vertical plane VP2 orthogonal to this vertical plane VP1.

Figure 15B:
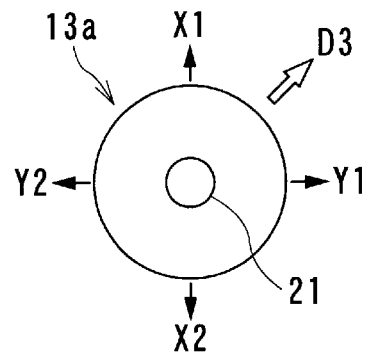

In FIG. 15B, a direction in which the lever 21 of the joystick 13a is set longitudinally corresponds to the X1 and X2 directions along the aforementioned vertical plane VP1; and a direction in which the lever 21 is set transversely corresponds to the Y1 and Y2 directions along the aforementioned vertical plane VP2, respectively. These position relationships can be easily recognized in the joystick 13a side by the operator by symbols or coloring and the like. In this manner, a position relationship between the direction in which the lever 21 of the joystick 13a is set and each of the vertical planes VP1 and VP2 is clarified.

Figure 15C:
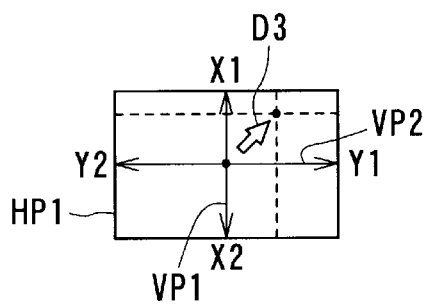

For example, in FIG. 15C, in the case where a cross line position (or region of interest) between the vertical planes VP1 and VP2 shown in FIGS. 15A and B is moved on the horizontal plane HP1 displayed on the monitor in a substantially intermediate direction between the X1 direction and the Y1 direction, it is evident immediately by referring to a display indicative of the X1 direction and Y1 direction on the joystick 13a that the lever 21 may be set to the right oblique front side shown in the figure on the joystick 13a.

Figure 15D:
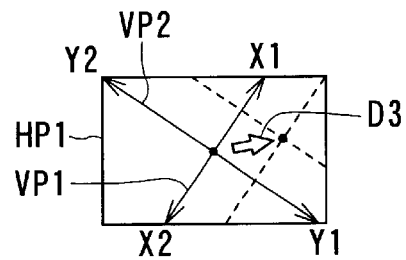

This also applies to a case in which the orientations of the vertical planes VP1 and VP2 are changed obliquely by rotation of the lever 21 of the joystick 13a as shown in FIG. 15D.

In FIG. 15D, the vertical planes VP1 and VP2 are rotated on the screen together with rotation of the joystick 13a. In this case, together with rotation of the joystick 13a, an ultrasonic image can be rotated without rotating the vertical planes VP1 and VP2.

Figure 15E:
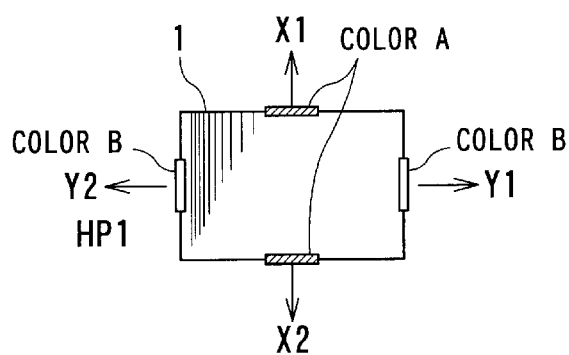

In addition, with respect to associating the direction of the plurality of planes with the joystick direction, as shown in FIG. 15E, the coloring such as colors A and B identifiable in the X1, X2, Y1, and Y2 directions or another identification is applied to the main body of the probe 1 as shown in FIG. 15E so as to utilize it.

In the illustrative embodiment, although there has been described a case in which a joystick is mainly used as an input device employed for region of interest (ROI) setting, FIG. 16A and FIG. 16B show an case in which a trackball 13b is employed as an example of the other device.

In a trackball 13b shown in FIG. 16A, the ball 30 of the trackball is moved, whereby the region of interest (or cross line position between vertical planes VP1 and VP2) is changed suitably on the aforementioned transverse plane HP1 shown in FIG. 16B, and the positions of the vertical planes VP1 and VP2 can be changed together with the changed position (Refer to the direction D4 in the figure.). In addition, an input section 31 capable of moving the position of the region of interest (ROI) in a direction (depth direction) orthogonal to the horizontal plane HP1 is provided in the vicinity of the trackball 13b shown in FIG. 16A.

In the illustrative embodiment, although an example of the ultrasonic diagnostic apparatus is described, the region of interest (ROI) setting means, plane position change means, and display image means or the like mounted on this apparatus are applicable to a case in which a variety of measurements are performed by using an image processing apparatus such as workstation after image acquisition. An example of the ultrasonic image processing apparatus is shown in FIG. 17.

An image processing apparatus 100 shown in FIG. 17 comprises a main body 101 and a monitor 102 connected to the main body. The main body 101 is equipped with a control unit 103 (incorporating a predetermined function required for measurement in the display unit 12); an operating unit 104 (incorporating a predetermined function required for measurement or the like of the inside of the operating panel 13); a joystick 105 having its function similar to the above; and a trackball 106 or the like.

In this manner, this image processing apparatus 100 inputs three-dimensional ultrasonic image data of the diagnosis site of the patient's body under the control of the control unit 103; obtains ultrasonic images of a plurality of planes with their difference orientations, thereby generating a display image thereof; sets a position of the region of interest (ROI) by operating the joystick 105 or the like; contrarily, changes a position of the plane so as to include this region of interest, changes a position of the plane; and sets a position of the region of interest (ROI) based on the positions of the plurality of planes.

In addition, in the illustrative embodiment, although a configuration is provided so as to set the region of interest or a plurality of planes after ultrasonic volume data has been acquired, as another example, the region of interest (ROI) or a plurality of planes are set and changed, and thereafter, only the corresponding planes can undergone ultrasonic scanning.

In this case, according to the ultrasonic diagnostic apparatus, the position of a region of interest (ROI) is set; the positions of plurality of planes with their different orientations are changed so as to include this region of interest (ROI); an ultrasonic wave is transmitted and received for the diagnosis site of the patient's body along the changed plurality of planes; and ultrasonic images of a plurality of planes are obtained, thereby making it possible to generate a display image thereof.

In addition, according to the ultrasonic diagnostic apparatus, the positions of a plurality of planes with their different orientations are changed; the position of a region of interest is set based on the positions of these plurality of planes; an ultrasonic wave is transmitted and received for the diagnosis region of the patient's body along the changed plurality of planes; and ultrasonic images of a plurality of planes are obtained, thereby making it possible to generate a display image thereof.

In the illustrative embodiment and the aforementioned description of the embodiments, when a region of interest (ROI) or a cross line position among plurality of planes is changed, although the positions of a plurality of planes including the region of interest or the positions of a plurality of planes forming the cross line are set in real time together with such change, the present invention is not limited thereto. For example, after the region of interest or the cross line position among a plurality of planes has been changed, a configuration can be provided so that the positions of a plurality of planes including the region of interest (ROI) or the positions of a plurality of planes forming the cross line position are set by manual operation such as pushing the button.

The description of the embodiments has now been completed. The present invention includes any suitable change or modification in configuration without departing the scope of claims in one skilled in the art without being limited to such embodied configuration.

What is claimed is:

1. An ultrasonic diagnostic apparatus comprising:
   an ultrasonic transmitter and receiver configured to transmit and receive an ultrasonic wave for a diagnosis site of a patient's body in a three-dimensional manner, thereby obtaining a receiving ultrasonic echo signal;
   a data generator configured to generate three-dimensional image data based on the ultrasonic echo signal obtained by the ultrasonic wave transmitted and received the ultrasonic transmitter and receiver;
   a display image generator configured to obtain ultrasonic images of a plurality of planes with different orientations based on the three-dimensional image data generated by the data generator, thereby generating a display image thereof;
   a controller configured to set a position of an ROI (region of interest) for a measurement required for an ultrasound Doppler or examination of the diagnosis part of the patient's body, and configured to change positions of the plurality of planes so as to include the ROI; and
   a measuring processor configured to perform the measurement based on the position of the ROI and to display a result of the measurement.

2. The ultrasonic diagnostic apparatus as claimed in claim 1, wherein the ROI is used for at least one of PW (Pulse Wave), CW (Continuous Wave), M-mode, CFM (Color Flow Mapping), TDI (Tissue Doppler Imaging), and image measurement.

3. The ultrasonic diagnostic apparatus as claimed in claim 1, wherein the position of the ROI and the positions of said plurality of planes are tracked with each other in real time.

4. The ultrasonic diagnostic apparatus as claimed in claim 1, wherein said plurality of planes are orthogonal to each other.

5. The ultrasonic diagnostic apparatus as claimed in claim 1, wherein said plurality of planes comprise a first plane substantially parallel to a scanning direction of said said ultrasonic wave, a second plane substantially parallel to a scanning direction of said ultrasonic wave and substantially orthogonal to said first plane, and a third plane substantially orthogonal to said first plane and said second plane, respectively.

6. The ultrasonic diagnostic apparatus as claimed in claim 5, wherein the controller comprises
   a joystick having:
   a lever configured to move at least in a longitudinal direction and a transverse direction, wherein the ROI moves on the first and the third planes when the lever moves in the longitudinal direction and the ROI moves on the second and the third planes when the lever moves in the transverse direction; and
   an input section mounted to the lever, wherein the ROI moves in a direction orthogonal to the third plane when the input section is operated.

7. The ultrasonic diagnostic apparatus as claimed in claim 1, wherein the controller comprises
   a trackball having:
   a ball, wherein the ROI moves on the third plane when the ball is operated; and
   an input section mounted in the vicinity of the ball, wherein the ROI moves in a direction orthogonal to the third plane when the input section is operated.

8. The ultrasonic diagnostic apparatus as claimed in claim 1, wherein:
   the ROI includes a position corresponding to a sample gate used for Pulse Wave Doppler or a position corresponding to a sample line used for Continuous Wave Doppler or M-mode imaging; and
   the measurement includes a measurement concerning an ultrasound Doppler frequency distribution on the ROI.

9. An ultrasonic diagnostic apparatus comprising:
   an ultrasonic transmitter and receiver configured to transmit and receive an ultrasonic wave for a diagnosis site of a patient's body in a three-dimensional manner, thereby obtaining a receiving ultrasonic echo signal;
   a data generator configured to generate three-dimensional image data based on the ultrasonic echo signal obtained by the ultrasonic wave transmitted and received by the ultrasonic transmitter and receiver;
   a display image generator configured to obtain ultrasonic images of a plurality of planes with different orientations based on said three-dimensional image data generated by the data generator, thereby generating a display image thereof;
   a controller configured to change the position of the plurality of planes, and configured to set a position of an ROI (region of interest) for a measurement required for an ultrasound Doppler or examination of the diagnosis site of the patient's body based on the positions of said plurality of planes; and
   a measuring processor configured to perform the measurement based on the position of the ROI and to display a result of the measurement.

10. The ultrasonic diagnostic apparatus as claimed in claim 9, wherein:
    the ROI includes a position corresponding to a sample gate used for Pulse Wave Doppler or a position corresponding to a sample line used for Continuous Wave Doppler or M-mode imaging; and
    the measurement includes a measurement concerning an ultrasound Doppler frequency distribution on the ROI.

11. An ultrasonic diagnostic apparatus comprising:
    a controller configured to set a position of an ROI (region of interest) for a measurement required for an ultrasound Doppler or examination of a diagnosis site of a patient's body, and configured to change positions of a plurality of planes with different orientations so as to include the ROI;

a display image generator configured to transmit and receive an ultrasonic wave for the diagnosis site of the patient's body along said plurality of planes changed by the controller, and obtaining ultrasonic images of said plurality of planes, thereby generating a display image thereof; and a measuring processor configured to perform the measurement based on the position of the ROI and to display a result of the measurement.

12. The ultrasonic diagnostic apparatus as claimed in claim 11, wherein:

the ROI includes a position corresponding to a sample gate used for Pulse Wave Doppler or a position corresponding to a sample line used for Continuous Wave Doppler or M-mode imaging; and the measurement includes a measurement concerning an ultrasound Doppler frequency distribution on the ROI.

13. An ultrasonic diagnostic apparatus comprising:

a controller configured to change positions of a plurality of planes with different orientations, and configured to set a position of an ROI (region of interest) for a measurement required for an ultrasound Doppler or examination of a diagnosis site of a patient's body based on the positions of the plurality of planes;

a display image generator configured to transmit and receive an ultrasonic wave for the diagnosis site of the patient's body along said plurality of planes changed by the controller, and obtaining ultrasonic images of said plurality of planes, thereby generating a display image thereof; and a measuring processor configured to perform the measurement based on the position of the ROI and to display a result of the measurement.

14. The ultrasonic diagnostic apparatus as claimed in claim 13, wherein:

the ROI includes a position corresponding to a sample gate used for Pulse Wave Doppler or a position corresponding to a sample line used for Continuous Wave Doppler or M-mode imaging; and the measurement includes a measurement concerning an ultrasound Doppler frequency distribution on the ROI.

15. An ultrasonic diagnostic apparatus comprising:

an ultrasonic transmitter and receiver configured to transmit and receive an ultrasonic wave for a diagnostic site of a patient's body in a three-dimensional manner, thereby obtaining an ultrasonic echo receiving signal;

a data generator configured to generate three-dimensional image data based on the ultrasonic echo signal obtained by the ultrasonic wave transmitted and received by the ultrasonic transmitter and receiver;

a display image generator configured to obtain ultrasonic images of a plurality of planes with different orientations based on said three-dimensional image data generated by the data generator, thereby generating a display image thereof;

a controller configured to set a cross line position of said plurality of planes, and configured to change positions of the plurality of planes so as to include said cross line position; and a measuring processor configured to perform a measurement based on the cross line position and to display a result of the measurement.

16. An ultrasonic diagnostic apparatus comprising:

an ultrasonic transmitter and receiver configured to transmit and receive an ultrasonic wave for a diagnostic site of a patient's body in a three-dimensional manner, thereby obtaining a receiving ultrasonic echo signal;

a data generator configured to generate three-dimensional image data based on the ultrasonic echo signal obtained by the ultrasonic wave transmitted and received by the ultrasonic transmitter and receiver;

a display image generator configured to obtain ultrasonic images of a plurality of planes with different orientations based on said three-dimensional image data generated by the data generator, thereby generating a display image thereof;

a controller configured to change positions of the plurality of planes, and configured to set a cross line position thereof based on positions of said plurality of planes; and a measuring processor configured to perform a measurement based on the cross line position and to display a result of the measurement.

17. An ultrasonic image processing apparatus comprising:

a display image generator configured to obtain ultrasonic images of a plurality of planes with different orientations based on three-dimensional ultrasonic image data of a diagnosis site of a patient's body;

a controller configured to set a position of a ROI (region of interest) for a measurement required for an ultrasound Doppler or examination of the diagnosis site of the patient's body, and configured to change a position of said planes so as to include the ROI; and a measuring processor configured to perform the measurement based on the position of the ROI and to display a result of the measurement.

18. The ultrasonic diagnostic apparatus as claimed in claim 17, wherein:

the ROI includes a position corresponding to a sample gate used for Pulse Wave Doppler or a position corresponding to a sample line used for Continuous Wave Doppler or M-mode imaging; and the measurement includes a measurement concerning an ultrasound Doppler frequency distribution on the ROI.

19. An ultrasonic image processing apparatus comprising:

a display image generator configured to obtain ultrasonic images of a plurality of planes with different orientations based on three-dimensional ultrasonic image data of a diagnosis site of a patient's body;

a controller configured to change a position of said plane, and configured to set a position of an ROI (region of interest) for a measurement required for an ultrasound Doppler or examination of the diagnosis site of the patient's body based on the positions of said plurality of planes; and a measuring processor configured to perform the measurement based on the position of the ROI and to display a result of the measurement.

20. The ultrasonic diagnostic apparatus as claimed in claim 19, wherein:

the ROI includes a position corresponding to a sample gate used for Pulse Wave Doppler or a position corresponding to a sample line used for Continuous Wave Doppler or M-mode imaging; and the measurement includes a measurement concerning an ultrasound Doppler frequency distribution on the ROI.

21. An ultrasonic diagnostic method comprising the steps of:
   transmitting and receiving an ultrasonic wave for a diagnosis site of a patient's body in a three-dimensional manner, thereby obtaining a receiving ultrasonic echo signal;
   generating three-dimensional image data based on the ultrasonic echo signal obtained by the ultrasonic wave transmitted and received by said transmitting and receiving step;
   obtaining ultrasonic images of a plurality of planes with different orientations based on the three-dimensional image data generated by said generating step, thereby generating a display image thereof;
   setting a position of an ROI (region of interest) for a measurement required for an ultrasound Doppler or examination of the diagnosis site of the patient's body;
   changing a position of the plane so as to include the ROI; and
   performing the measurement based on the position of the ROI and displaying a result of the measurement.

22. The ultrasonic image processing method in claim 21, wherein:
   the ROI includes a position corresponding to a sample gate used for Pulse Wave Doppler or a position corresponding to a sample line used for Continuous Wave Doppler or M-mode imaging; and
   the measurement includes a measurement concerning an ultrasound Doppler frequency distribution on the ROI.

23. An ultrasonic diagnostic method comprising the steps of:
   transmitting and receiving an ultrasonic wave for a diagnosis site of a patient's body in a three-dimensional manner, thereby obtaining a receiving ultrasonic echo signal;
   generating three-dimensional image data based on the ultrasonic echo signal obtained by the ultrasonic wave transmitted and received by said transmitting and receiving step;
   obtaining ultrasonic images of a plurality of planes with different orientations based on said three-dimensional image data generated by said generating step, thereby generating a display image thereof;
   changing a position of said plane;
   setting a position of an ROI (region of interest) for a measurement required for an ultrasound Doppler or examination of the diagnosis site of the patient's body based on positions of said plurality of planes; and
   performing the measurement based on the position of the ROI and displaying a result of the measurement.

24. The ultrasonic image processing method in claim 23, wherein:
   the ROI includes a position corresponding to a sample gate used for Pulse Wave Doppler or a position corresponding to a sample line used for Continuous Wave Doppler or M-mode imaging; and
   the measurement includes a measurement concerning an ultrasound Doppler frequency distribution on the ROI.

25. An ultrasonic diagnostic method comprising the steps of:
   setting a position of an ROI (region of interest) for a measurement required for an ultrasound Doppler or examination of a diagnosis site of a patient's body;
   changing positions of a plurality of planes with different orientations so as to include said region of interest;
   transmitting and receiving an ultrasonic wave for the diagnosis site of the patient's body along said plurality of planes changed by said changing step, and obtaining ultrasonic images of said plurality of planes, thereby generating a display image thereof; and
   performing the measurement based on the position of the ROI and displaying a result of the measurement.

26. The ultrasonic image processing method in claim 25, wherein:
   the ROI includes a position corresponding to a sample gate used for Pulse Wave Doppler or a position corresponding to a sample line used for Continuous Wave Doppler or M-mode imaging; and
   the measurement includes a measurement concerning an ultrasound Doppler frequency distribution on the ROI.

27. An ultrasonic diagnostic method comprising the steps of:
   changing positions of a plurality of planes with different orientations;
   setting a position of an ROI (region of interest) for a measurement required for an ultrasound Doppler or examination of a diagnosis site of a patient's body based on the positions of said plurality of planes;
   transmitting and receiving an ultrasonic wave for the diagnosis site of the patient's body along said plurality of planes changed by said changing step, and obtaining ultrasonic images of said plurality of planes, thereby generating a display image thereof; and
   performing the measurement based on the position of the ROI and displaying a result of the measurement.

28. The ultrasonic image processing method in claim 27, wherein:
   the ROI includes a position corresponding to a sample gate used for Pulse Wave Doppler or a position corresponding to a sample line used for Continuous Wave Doppler or M-mode imaging; and
   the measurement includes a measurement concerning an ultrasound Doppler frequency distribution on the ROI.

29. An ultrasonic diagnostic method comprising the steps of:
   transmitting and receiving an ultrasonic wave for a diagnostic site of a patient's body in a three-dimensional manner, thereby obtaining an ultrasonic echo receiving signal;
   generating three-dimensional image data based on the ultrasonic echo signal obtained by the ultrasonic wave transmitted and received by said transmitting and receiving step;
   obtaining ultrasonic images of a plurality of planes with different orientations based on said three-dimensional image data generated by said generating step, thereby generating a display image thereof;
   setting a cross line position of said plurality of planes;
   changing positions of the plurality of planes so as to include said cross line position; and
   performing a measurement based on the cross line position and displaying a result of the measurement.

30. An ultrasonic diagnostic method comprising:
   transmitting and receiving an ultrasonic wave for a diagnostic site of a patient's body in a three-dimensional manner, thereby obtaining a receiving ultrasonic echo signal;
   generating three-dimensional image data based on the ultrasonic echo signal obtained by the ultrasonic wave transmitted and received by said transmitting and receiving step;

obtaining ultrasonic images of plurality of planes with different orientations based on said three-dimensional image data generated by said data generating step, thereby generating a display image thereof;

changing a position of the plane;

setting a cross line position thereof based on positions of said plurality of planes; and performing a measurement based on the cross line position and displaying a result of the measurement.

31. An ultrasonic image processing method comprising the steps of:

obtaining ultrasonic images of a plurality of planes with different orientations based on three-dimensional ultrasonic image data of a diagnosis of a patient's body;

setting a position of an ROI (region of interest) for a measurement required for an ultrasound Doppler or examination of the diagnosis site of the patient's body;

changing a position of said planes so as to include the ROI; and performing the measurement based on the position of the ROI and displaying a result of the measurement.

32. The ultrasonic image processing method in claim 31, wherein:

the ROI includes a position corresponding to a sample gate used for Pulse Wave Doppler or a position corresponding to a sample line used for Continuous Wave Doppler or M-mode imaging; and the measurement includes a measurement concerning an ultrasound Doppler frequency distribution on the ROI.

33. An ultrasonic image processing method comprising the steps of:

obtaining ultrasonic images of a plurality of planes with different orientations based on three-dimensional ultrasonic image data of a diagnosis site of a patient's body;

changing a position of said plane;

setting a position of an ROI (region of interest) for a measurement required for an ultrasound Doppler or examination of the diagnosis site of the patient's body based on the positions of said plurality of planes; and performing the measurement based on the position of the ROI and displaying a result of the measurement.

34. The ultrasonic image processing method in claim 33, wherein:

the ROI includes a position corresponding to a sample gate used for Pulse Wave Doppler or a position corresponding to a sample line used for Continuous Wave Doppler or M-mode imaging; and the measurement includes a measurement concerning an ultrasound Doppler frequency distribution on the ROI.

* * * * *